United States Patent [19]

Maurer et al.

[11] Patent Number: 5,370,671
[45] Date of Patent: Dec. 6, 1994

[54] INCONTINENCE ELECTRODE APPARATUS

[75] Inventors: Donald D. Maurer, Marine on the St. Croix; Mary M. Lien, Arden Hills, both of Minn.

[73] Assignee: Empi, Inc., St. Paul, Minn.

[21] Appl. No.: 10,665

[22] Filed: Jan. 28, 1993

Related U.S. Application Data

[63] Continuation-in-part of Ser. No. 675,568, Mar. 26, 1991, Pat. No. 5,199,443, and a continuation-in-part of Ser. No. 975,518, Nov. 12, 1992.

[51] Int. Cl.$^5$ ............................ A61N 1/05; A61N 1/36
[52] U.S. Cl. ........................................ 607/41; 607/138
[58] Field of Search ................... 607/39, 40, 41, 138, 607/66

[56] References Cited

U.S. PATENT DOCUMENTS

| | | | |
|---|---|---|---|
| 1,253,955 | 1/1918 | Galligan . | |
| 1,704,000 | 3/1929 | Herwig et al. . | |
| 2,085,644 | 6/1937 | Fericot | 128/407 |
| 2,126,257 | 8/1938 | Hird | 128/303.11 |
| 3,403,684 | 10/1968 | Stiebel et al. | 128/407 |
| 3,749,100 | 7/1973 | Von Der Mosel | 128/407 |
| 4,124,028 | 11/1978 | Gallo | 128/407 |
| 4,406,288 | 9/1986 | Horwinski et al. | 128/422 |
| 4,564,024 | 1/1986 | Wohler, Jr. | 128/788 |
| 4,688,575 | 8/1987 | DuVall | 128/422 |
| 4,881,526 | 11/1989 | Johnson et al. | 128/24.5 |
| 4,909,263 | 3/1990 | Norris | 128/788 |
| 5,117,840 | 6/1992 | Brenman et al. | 128/788 |
| 5,199,443 | 4/1993 | Maurer et al. | 607/138 |
| 5,213,097 | 5/1993 | Zeindler | 128/401 |
| 5,233,987 | 8/1993 | Fabian et al. | 607/41 |

FOREIGN PATENT DOCUMENTS 2822616  11/1979  Germany ............................ 607/138

OTHER PUBLICATIONS

Empi, Inc., *INNOVA Feminine Incontinence Treatment System Design Rationale*, 1992.
Empi, Inc., *INNOVA*, 1991, 1992.
*Intravaginal Stimulation for Urinary Incontinence Selected Abstracts*.
Ivan A. Brezovich, Ph. D.; Michael B. Lilly, M.D.; John R. Durant, M.D.; and Diane B. Richards, R.N.; *A Practical System for Clinical Radiofrequency Hyperthermia*, Mar., 1981, vol. 7, pp. 423–430.
Hopkinson, B. R. et al., "Electrical Treatment of Anal Incontinence", *The Lancet*, Feb. 5, 1966, pp. 297–298.

*Primary Examiner*—Lee S. Cohen
*Attorney, Agent, or Firm*—Kinney & Lange

[57] ABSTRACT

An incontinence electrode for controlling urinary incontinence in women is made of alternating regions of conductive and non-conductive polymers molded to form a flexible tubular body. Electrical leads couple the conductive regions to an electrical stimulation controller. The controller provides electrical current to the conductive regions at two different frequencies to cause a contraction of the vaginal muscles responsible for controlling urinary incontinence in women. The conductive regions have a volume resistivity which closely approximates the impedance of vaginal tissue, thereby substantially eliminating current density burns to the vaginal tissue.

18 Claims, 1 Drawing Sheet

INCONTINENCE ELECTRODE APPARATUS

REFERENCE TO CO-PENDING APPLICATION

The present application is a continuation-in-part of U.S. patent application Ser. No. 07/675,568 filed Mar. 26, 1991, now U.S. Pat. No. 5,199,443, entitled INCONTINENCE ELECTRODE APPARATUS AND METHOD, by Donald D. Maurer et al.

The present application is also a continuation-in-part U.S. patent application Ser. No. 07/975,518 filed Nov. 12, 1992, entitled ELECTRODE FOR ACTIVATING PELVIC REFLEXES, by Donald D. Maurer et al.

BACKGROUND OF THE INVENTION

The present invention relates generally to the field of electrical neuromuscular stimulation for the treatment of urinary incontinence in women. In particular, the present invention is a molded vaginal electrode having increased effectiveness, an improved method of construction and increased safety.

Electrical neuromuscular stimulation is widely used to assist persons afflicted with motor dysfunctions in performing muscle contraction maneuvers. Motor nerve fibers are electrically stimulated by means of transcutaneously applied pulses of electrical current to cause contraction of the innervated muscles. This technique is also used to re-educate patients in the proper use of the dysfunctional muscles.

For example, in cases in which urinary incontinence in women is caused by the patient's inability to properly contract the external sphincter of the urethra, it has been shown that neuromuscular stimulation of the dysfunctional muscles by means of a vaginal or anal electrode can effectively prevent the unwanted flow of urine. Through the use of such an electrode, some patients can educate themselves to voluntarily or automatically impede the flow of urine.

A more important application of the pelvic floor stimulation is the exercise and toning of the muscles of the pelvic floor which support the bladder, vagina, urethra and other organs. Muscles which have become lax or stretched through the processes of childbirth or natural aging, can be strengthened and tightened to properly support these structures, thus affecting positively the patient's ability to maintain continence. Another common form of incontinence in women is called urge incontinence. This condition results either from an irritable bladder or a hyperactive bladder muscle. Electrical stimulation can activate certain reflexes which inhibit the inappropriate bladder contractions ("urgency") associated with urge incontinence.

Electrical stimulators for controlling urinary incontinence generally include a relatively rigid vaginal plug with one or more electrodes in the form of conductive metal rings. A lead harness extends from the plug to a controller or stimulator which generates stimulation signals. The controller is usually worn externally, attached to the user's clothing.

Proper positioning of the electrode within the vagina is essential to deliver current to the motor nerve intended to be affected. Incorrect positioning may result in reduced efficiency of stimulation. Furthermore, the size, shape and weight of the electrode affect the retainability of the proper position of the electrode.

Vaginal electrodes which are relatively rigid cause compression of blood vessels which supply the contracting pelvic muscles, and compression of pressure sensors in the vaginal tissue during contraction. This results in an undesirable anaerobic and uncomfortable contraction.

The use of metal for the conductive bands of vaginal plugs also has some drawbacks. Metallic conductors of vaginal electrodes known in the art have an impedance substantially lower than that of vaginal tissue. When this type of impedance relationship exists, the current density tends to be greatest at the edge of the conductive ring. This "edge effect" can result in burns of the tissue in contact with the conductor if the current reaches a high enough intensity. The severity of the "edge effect" is proportional to the impedance differential between the conductor and the tissue with which it is in contact. Therefore, the use of such vaginal electrodes with metallic conductors can potentially cause pain, discomfort and injury to the patient.

Integrity problems generally plaque the coupling of the electrical leads to conductive polymers. Overmolding of tabs, rings or stripped wires during the molding process is a typical method of establishing contact. This connection method, however, has proved ineffective. Various factors can contribute to diminished contact integrity between the metal and conductive polymer thereby increasing the electrical impedance and decreasing the effectiveness of the electrode. These factors include heat-induced pull-away of the polymeric compounds from the metal contacts during the molding process, "stress creep" (elastomeric relaxation) of the polymeric compounds, flexing of the vaginal electrode due to contractions of the vaginal muscles, and corrosive attack of the surface of the metal by catalysts or other residuals in the polymer.

Vaginal electrodes known in the art deliver electrical signals to the vaginal musculature by means of a single channel. The limitation of providing a therapeutic signal at a single frequency band per therapy session theoretically compromises the effectiveness of treatment. Optimum treatment of stress incontinence has been shown to involve delivery of a frequency and amplitude of current different than the optimum frequency and current amplitude recommended for the treatment of urge incontinence.

There is a continuing need for lightweight, flexible vaginal electrodes which can prevent the unwanted flow of urine, and which can retrain the dysfunctional muscles responsible for stress and urge incontinence. In addition to being effective, the electrode must be durable, hygienical and inexpensive to manufacture.

SUMMARY OF THE INVENTION

The present invention is a flexible vaginal electrode adapted to be inserted into a woman's vagina for stimulating and constricting the pelvic muscles to retrain the muscles and to prevent the flow of urine through the urethra. The vaginal electrode includes a relatively short tubular body, which is molded from relatively compliant polymers. The tubular body includes first, second and third conductive annular regions which are formed by incorporating conductive materials into the polymer. The conductive polymer has an impedance closely matching that of vaginal tissue, which substantially eliminates the "edge effect" of each annular electrode and its attendant burning effect. The annular electrodes are longitudinally spaced and integrally formed with non-conductive polymer to form the tubular body. Stimulation means communicate with the annular electrodes and provide electrical signals necessary to contract the pelvic muscles. The tubular design and the polymeric construction combine to create a comfortable, relatively flexible vaginal electrode which permits efficient contraction of muscle fibers of the pelvic musculature while substantially eliminating compression of blood vessels and pressure sensors of the vaginal tissue. This results in a comfortable, enhanced conditioning of the muscles responsible for preventing urge incontinence and stress incontinence.

In a preferred embodiment, the stimulation means provides dual channel stimulation to the vaginal electrode for enhanced toning of the two muscle groups responsible for urge and stress incontinence. A first electrical signal having a first frequency is delivered to the first annular region for stimulation of the muscles of the pelvic floor. Additionally, a second electrical signal having a second frequency different than the first frequency is delivered to the second annular region for inhibition of contractions of the bladder wall. The third annular electrode provides a common electrode for the first and second electrical signals. This embodiment allows the vaginal electrode to have a reduced size and weight, which aids in maintaining the vaginal electrode in the proper position.

The vaginal electrode of the present invention provides enhanced comfort due to impedance matching of the conductive polymer electrodes and surrounding tissue and a more flexible tubular body construction. Moreover, the vaginal electrode of the present invention is able to provide specialized dual channel conditioning of the two muscle groups responsible for controlling urge and stress incontinence.

DETAILED DESCRIPTION OF THE PREFERRED EMBODIMENTS

Figure 1:
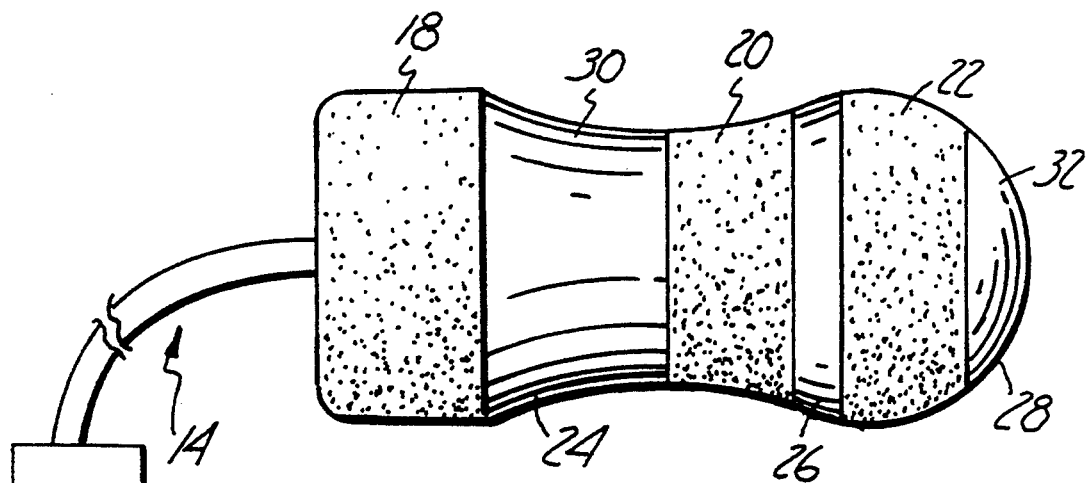
FIG. 1 is a side view of the electrical neuromuscular stimulator of the present invention.

FIG. 1 is a side view of electrical neuromuscular stimulator 10 of the present invention. Neuromuscular stimulator 10 generally includes vaginal electrode 12, electrical lead harness 14 and electrical stimulation controller 16. Vaginal electrode 12 includes conductive regions 18, 20 and 22, and non-conductive regions 24, 26 and 28. Conductive regions 18, 20 and 22 are electrically coupled to controller 16 by leads (not shown) contained within lead harness 14.

As shown in FIG. 1, vaginal electrode 12 has an hourglass-like shape with outer surface 30 being radially tapered through regions 24, 20 and 26. Further, regions 26, 22 and 28 are contoured to provide a bulbous end 32, which facilitates atraumatic insertion of vaginal electrode 12 within a vagina. With vaginal electrode 12 positioned within the vagina adjacent the dysfunctional pelvic muscles, electrical current from controller 16 is delivered to conductive regions 18, 20 and 22. This electrical current causes the pelvic muscles to contract causing the vaginal wall to bear down on vaginal electrode 12 in a non-uniform manner so as to conform to the hourglass shape of exterior surface 30. The hourglass shape of vaginal electrode 12 thereby aids in maintaining vaginal electrode 12 in the desired location.

Conductive regions 18, 20 and 22 are preferably formed from Carbon-loaded Silicone Rubber Rhône-Poulenc RS-1516, while non-conductive regions 24, 26 and 28 are formed from a non-conductive polymer, such as Dow-Corning SILASTIC ® Q7-4535. Vaginal electrode 12 is fabricated by a molding process, in which annular bands forming conductive regions 18, 20 and 22 are positioned along a mandril (not shown) to achieve a desired spacing. The mandril and the positioned conductive regions 18, 20 and 22 are then inserted into a second mold into which the non-conductive polymer is injected to connect conductive regions 18, 20 and 22 to non-conductive regions 24, 26 and 28. Vaginal electrode 12 is then cured to effect the chemical bonding of conductive regions 18, 20 and 22 to non-conductive regions 24, 26 and 28.

Conductive regions 18, 20 and 22 have a volume resistivity of between about 1 to about 2500 ohm-centimeters, which approximates the volume resistivity of vaginal tissue. In a preferred embodiment, the volume resistivity of conductive regions 18, 20 and 22 ranges from about 5 to about 20 ohm-centimeters. Due to the close match of the impedance between conductive regions 18, 20 and 22 and vaginal tissue, vaginal electrode 12 substantially eliminates "edge effect" current density burns to the vaginal tissue, thereby providing the most comfortable therapy session for a patient.

Controller 16 simultaneously provides dual channel stimulation to conductive regions 18, 20 and 22. A first channel pulse signal at a frequency of between about 5 Hz to about 20 Hz is supplied between regions 18 and 22. A second channel pulse signal at a frequency of between about 30 Hz to about 100 Hz is supplied between regions 20 and 22. In a preferred embodiment, the first channel pulse signal is about 10 Hz, and the second channel pulse is about 50 Hz. Each signal is specialized for stimulating an appropriate reflex pathway. Dual channel stimulation of pelvic floor muscles provides a therapy which is adaptable to urge incontinence, stress incontinence or a combination of the two forms of incontinence.

Figure 2:
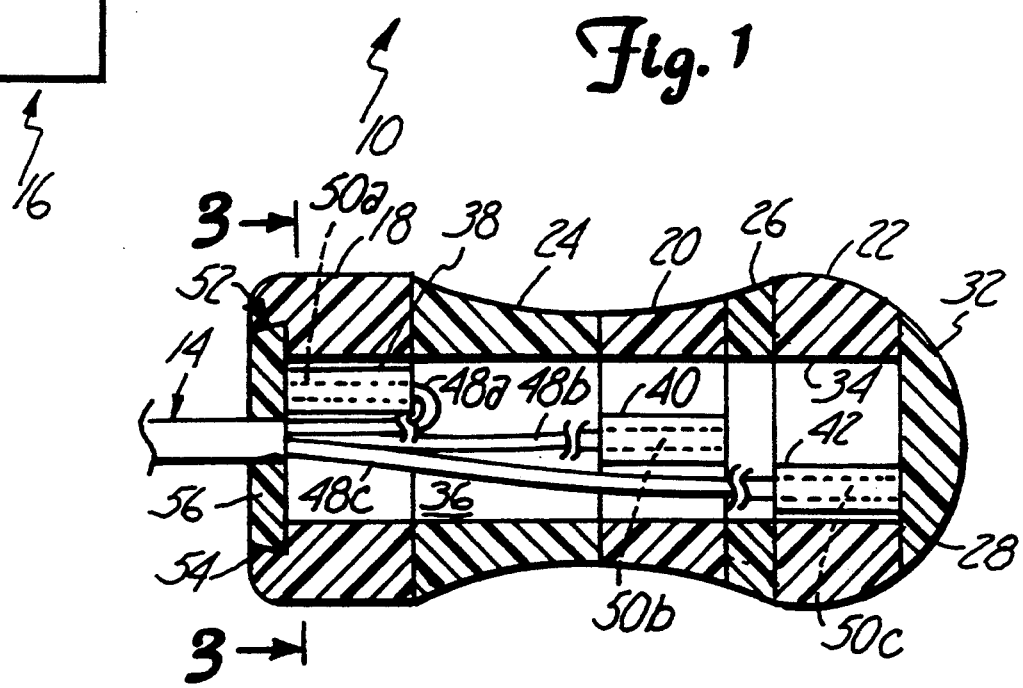
FIG. 2 is a longitudinal sectional view of the vaginal electrode of FIG. 1 taken along line 2—2.
Figure 3:
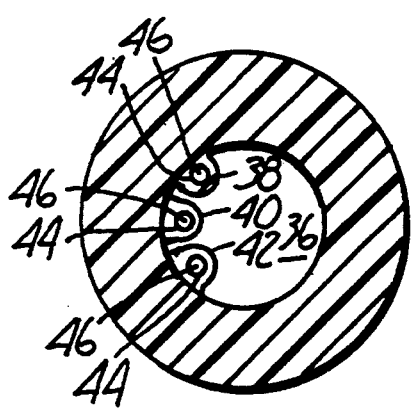
FIG. 3 is a cross-sectional view of the vaginal electrode of FIG. 1 taken along line 3—3.

FIG. 2 is a longitudinal section view of vaginal electrode 12 taken along line 2—2 of FIG. 1. Vaginal electrode 12 has an interior circumferential surface 34, which defines inner cavity 36 of vaginal electrode 12. Inner cavity 36 has an inner diameter of about 0.500 inches. Inner surface 34 of conductive regions 18, 20 and 22 includes receptacles 38, 40 and 42, respectively. As shown in FIGS. 2 and 3, receptacles 38, 40 and 42 include domed regions 44 and cylindrical cavities 46. Each cavity 46 has a diameter of about 0.070 inches and a longitudinal axis which is parallel to inner surface 34 of vaginal electrode 12. In a preferred embodiment, receptacle 40 is radially offset about 50° from receptacle 38, and receptacle 42 is radially offset about 50° from receptacle 40. This orientation permits easy electrical connection to controller 16. As further shown in FIGS. 2 and 3, vaginal electrode 12 has a generally tubular shape.

As shown in FIG. 2, vaginal electrode 12 is coupled to controller 16 by electrical leads 48a–48c, which are housed inside lead harness 14. Leads 48a–48c terminate in a pin-type connector 50a–50c, respectively. Pin connectors 50a–50c are formed of metal, such as gold-coated brass, and have a diameter of about 0.01 inches larger than cavity 46 of receptacles 38, 40 and 42. Pin connectors 50a–50c are attached to leads 48a–48c by any acceptable manner, such as crimping and/or soldering. Pin connectors 50a–50c are inserted within cavity 46 of receptacles 38, 40 and 42, respectively. Because the diameter of each pin connector 50a–50c is slightly larger than the diameter of cavity 46 of receptacles 38, 40 and 42, electrical connection of leads 48a–48c is accomplished by a durable and reliable mechanical tension. Thus, despite "stress creep" (elastomeric relaxation) of the polymer compounds of vaginal electrode 12, flexing of vaginal electrode 12 due to the contractive forces of the vaginal muscles, or swelling of the polymer compounds of vaginal electrode 12 due to the absorption of vaginal fluids, the connection of pin connectors 50a–50c to receptacles 38, 40 and 42, provides a continuous mechanical and electrical contact.

In the preferred embodiment, vaginal electrode 12 has length ranging from about 1.75 to about 2.50 inches. This reduced length is especially beneficial for geriatric patients with some degree of atrophy or with those with a truncated vagina. In addition, vaginal electrode 12 has a weight ranging from about 20 to about 30 grams, which aids in the retention of the electrode within the vagina. Finally, vaginal electrode 12 preferably has a wall thickness of about 0.20 inch to about 0.55 inch and an outer diameter of about 0.65 inch to about 1.10 inch. As measured from left to right as shown in FIG. 2, conductive region 18 has a width of about 0.516 inches, conductive region 20 has a width of about 0.400 inches, and conductive region 22 has a width of about 0.150 inches. Non-conductive region 24 has a width of about 0.600 inches, non-conductive region 26 has a minimum width of about 0.115 inches, and non-conductive region 28 has a width of about 0.185 inches.

In a preferred embodiment, vaginal electrode 12 has a durometer of between 40 to 90 shore A, with a durometer of between about 40 to 60 shore A being most preferable. The generally tubular shape of vaginal electrode 12 coupled with the relatively soft durometer of conductive regions 18, 20 and 22, and non-conductive regions 24, 26 and 28 ensures that vaginal electrode 12 is radially flexible. The radial flexibility of vaginal electrode 12 permits the vaginal musculature to contract against vaginal electrode 12 with minimal compression of pressure sensors in the vaginal tissue. This results in improved comfort for the patient. In addition, the radial flexibility of vaginal electrode 12 allows for a more natural dynamic, rather than isometric, contraction. Vaginal electrode 12 thereby substantially improves the treatment for urge and stress incontinence. Finally, capillary compression, which is common when pelvic floor muscles contract around a rigid vaginal electrode, results in reduced blood flow to the muscles and therefore an anaerobic contraction. The radial flexibility of vaginal electrode 12 helps avoid muscle fatigue caused by an anaerobic contraction by substantially preventing capillary compression when the pelvic floor muscles contract around vaginal electrode 12.

As further shown in FIG. 2, conductive region 18 includes recessed void 52 with radially tapered wall 54. Recessed void 52 accepts an end cap 56, which seals leads 48a–48c within cavity 36 of vaginal electrode 12. End cap 56 is preferably bonded within recessed void 52 with a suitable medical grade adhesive.

In an alternative embodiment, conductive regions 18, 20 and 22 are formed from a medical grade thermoplastic rubber such as SANTOPRENE® of Advanced Elastomer Systems. In yet another embodiment, conductive regions 18, 20 and 22 are formed from a medical grade thermoplastic rubber such as KRATON® of Shell Chemical Company.

Vaginal electrode 12 is comfortably adapted for the specific needs of a variety of patients. The soft polymeric construction substantially eliminates the compression of blood vessels and pressure sensors of the vaginal tissue upon contraction of the vaginal muscles. Furthermore, the reduced length of vaginal electrode 12 is well adapted for geriatric patients or patients with a truncated vagina. The reduced length of vaginal electrode 12 also accounts for a relatively low weight of vaginal electrode 12, which aids in its retention within a vagina. In addition, vaginal electrode 12 is capable of simultaneously stimulating the vaginal musculature at two different frequencies, which provides specialized conditioning of the muscle groups responsible for controlling urge and stress incontinence.

Although the present invention has been described with reference to preferred embodiments, workers skilled in the art will recognize that changes may be made in form and detail without departing from the spirit and scope of the invention.

What is claimed is:

1. An electrical stimulation system for controlling urinary incontinence comprising:
    an elongated tubular body having an interior surface and an exterior surface, the tubular body further having first, second and third conductive regions, each conductive region having a volume resistivity in the range of approximately 1 to 2500 ohm-centimeters and separated by at least one non-conductive region, the first, second and third conductive regions configured to provide a first current path and a second current path, wherein the first and second current paths share one of the conductive regions; and
    electrical stimulation means communicating with the first, second and third conductive regions, for delivering a first signal at a first frequent to the first current path, and for delivering a second signal at a second frequency, different from the first frequency, to the second current path.

2. The electrical stimulation system of claim 1 wherein the first frequency is between about 5 Hz to about 20 Hz.

3. The electrical stimulation system of claim 2 wherein the second frequency is about 30 Hz to about 100 Hz.

4. The electrical stimulation system of claim 1 wherein the tubular body has a length of about 1.75 to about 2.50 inches.

5. The electrical stimulation system of claim 1 wherein the elongated tubular body has a durometer of between about 40 to about 90 shore A.

6. The electrical stimulation system of claim 5 wherein the elongated tubular body has a durometer of between about 40 to about 60 shore A.

7. The electrical stimulation system of claim 1 wherein the elongated tubular body has a weight of about 20 to about 30 grams.

8. The electrical stimulation system of claim 1 and further comprising first, second, and third receptacles positioned on the interior surface of the elongated tubular body such that the first, second, and third receptacles are in contact with the first, second, and third conductive regions, respectively.

9. The electrical stimulation system of claim 8 wherein the second receptacle is radially offset by approximately 50 degrees from the first receptacle, and the third receptacle is radially offset by approximately 50 degrees from the second receptacle.

10. A dual channel stimulating system for controlling urinary incontinence comprising:

an elongated tubular body, having first, second and third conductive regions longitudinally spaced along the tubular body, each conductive region having a volume resistivity in the range of approximately 1 to 2500 ohm-centimeters and separated from an adjacent conductive region by at least one non-conductive region; and electrical stimulation means communicating with the first, second and third conductive regions for delivering a first signal at a first frequency to the first and third conductive regions, and for delivering a second signal at a second frequent, different from the first frequency, to the first and second conductive regions.

11. The stimulating system of claim 10 wherein the first frequency is between about 5 Hz to about 20 Hz.

12. The stimulating system of claim 10 wherein the second frequency is between about 30 Hz to about 100 Hz.

13. The stimulating system of claim 10 wherein the tubular body has a length of about 1.75 to about 2.50 inches.

14. The stimulating system of claim 10 wherein the elongated tubular body has a durometer of about 40 to about 90 shore A.

15. The stimulating system of claim 10 wherein the elongated tubular body has a durometer of about 40 to about 60 shore A.

16. The stimulating system of claim 10 wherein the elongated tubular body has a weight of about 20 to about 30 grams.

17. The electrical stimulating system of claim 10 and further comprising first, second, and third receptacles positioned on the interior surface of the elongated tubular body such that the first, second, and third receptacles are contact with the first, second, and third conductive regions, respectively.

18. The electrical stimulating system of claim 17 wherein the second receptacle is radially offset by approximately 50 degrees from the first receptacle, and the third receptacle is radially offset by approximately 50 degrees from the second receptacle.

* * * * *

UNITED STATES PATENT AND TRADEMARK OFFICE
CERTIFICATE OF CORRECTION

PATENT NO. : 5,370,671

DATED : December 6, 1994

INVENTOR(S) : DONALD D. MAURER, MARY M. LIEN

It is certified that error appears in the above-indentified patent and that said Letters Patent is hereby corrected as shown below:

Col. 7, line 19, delete "frequent", insert --frequency--

Signed and Sealed this

Twenty-first Day of March, 1995

Attest:

BRUCE LEHMAN

Attesting Officer     Commissioner of Patents and Trademarks